(12) United States Patent
Xie et al.

(10) Patent No.: US 9,149,416 B1
(45) Date of Patent: Oct. 6, 2015

(54) HIGH DEPOSITION CLEANSING SYSTEM

(75) Inventors: Min Xie, Plano, TX (US); Robin Rudolph, Grand Prairie, TX (US); Stephanie Ponder, Plano, TX (US)

(73) Assignee: WELLMARK INTERNATIONAL, Schaumburg, IL (US)

( * ) Notice: Subject to any disclaimer, the term of this patent is extended or adjusted under 35 U.S.C. 154(b) by 714 days.

(21) Appl. No.: 12/545,771

(22) Filed: Aug. 21, 2009

Related U.S. Application Data

(60) Provisional application No. 61/091,320, filed on Aug. 22, 2008.

(51) Int. Cl.
| | | |
|---|---|---|
| *A61K 8/00* | (2006.01) | |
| *C11D 1/65* | (2006.01) | |
| *C11D 3/43* | (2006.01) | |
| *C11D 1/12* | (2006.01) | |

(52) U.S. Cl.
CPC ... *A61K 8/00* (2013.01); *C11D 1/12* (2013.01); *C11D 1/65* (2013.01); *C11D 3/43* (2013.01)

(58) Field of Classification Search
CPC .............. C11D 1/38; C11D 1/02; C11D 1/12; C11D 1/62; C11D 1/65; C11D 3/00; C11D 3/0031; C11D 3/43; C11D 3/48
USPC ......... 510/119, 131, 160, 275, 405, 417, 418, 510/461; 424/405
See application file for complete search history.

(56) References Cited

U.S. PATENT DOCUMENTS

| | | | |
|---|---|---|---|
| 4,518,593 A | 5/1985 | Juvin et al. | |
| 4,584,319 A | 4/1986 | Lover et al. | |
| 4,997,642 A * | 3/1991 | Curtis et al. | ................... 514/521 |
| 5,151,269 A | 9/1992 | Greenshields et al. | |
| 5,326,484 A * | 7/1994 | Nakashima et al. | ............. 516/29 |
| 5,380,756 A | 1/1995 | Andrews et al. | |
| 5,610,186 A | 3/1997 | Workman | |
| 5,612,047 A * | 3/1997 | Duffy et al. | ................... 424/405 |
| 5,826,546 A | 10/1998 | Epstein | |
| 5,846,905 A * | 12/1998 | Frisch et al. | ................... 504/364 |
| 5,866,152 A | 2/1999 | Takebayashi et al. | |
| 6,130,253 A | 10/2000 | Franklin et al. | |
| 6,165,450 A * | 12/2000 | Chaudhuri et al. | ............. 424/59 |
| 6,500,446 B1 | 12/2002 | Derrieu et al. | |
| 7,109,240 B2 | 9/2006 | Bessette et al. | |
| 7,132,448 B2 | 11/2006 | Cottrell et al. | |

(Continued)

FOREIGN PATENT DOCUMENTS

| | | | |
|---|---|---|---|
| EP | 0 262 885 A2 | 4/1988 | |
| EP | 1 210 877 A1 * | 6/2002 | ............. A01N 25/02 |

OTHER PUBLICATIONS

Material Safety Data Sheet, Zinc oxide MSDS, Sciencelab.com, Inc., 6 pages.

*Primary Examiner* — Jane L Stanley
(74) *Attorney, Agent, or Firm* — Kilpatrick Townsend & Stockton LLP

(57) ABSTRACT

The present invention provides an insecticidal emulsion cleansing system comprising a clear oil-in-water (o/w) emulsion wherein the oil phase contains an ionic surfactant and an insecticide suspended together as nanometer sized particles in the water phase; and wherein the water phase contains an oppositely charged polymer. The insecticide is preferably a pyrethroid such as a natural pyrethrin or a synthetic pyrethroid. Suitable pyrethroids include pyrethroid esters and pyrethroid ethers.

18 Claims, 2 Drawing Sheets

(56) References Cited

U.S. PATENT DOCUMENTS

| | | | |
|---|---|---|---|
| 2002/0098221 A1* | 7/2002 | Taranta et al. | 424/405 |
| 2005/0034632 A1* | 2/2005 | Argillier et al. | 106/205.6 |
| 2005/0245582 A1 | 11/2005 | Cottrell et al. | |
| 2006/0045861 A1 | 3/2006 | Bejger et al. | |
| 2007/0020304 A1* | 1/2007 | Tamarkin et al. | 424/405 |
| 2008/0125480 A1* | 5/2008 | Pedersen et al. | 514/449 |
| 2008/0300313 A1* | 12/2008 | Byrne et al. | 514/611 |
| 2009/0018057 A1* | 1/2009 | Lambert et al. | 514/11 |

* cited by examiner

HIGH DEPOSITION CLEANSING SYSTEM

CROSS-REFERENCE TO RELATED APPLICATIONS

This application claims priority to U.S. Provisional Application No. 61/091,320, filed Aug. 22, 2008, the teaching of which is hereby incorporated by reference in its entirety for all purposes.

BACKGROUND OF THE INVENTION

This invention relates to an insecticide composition for use especially as a cleansing system, and intended in particular for destroying and repelling particularly resistant insects such as fleas and ticks. Generally, the topical insecticide formulations of the present invention are suitable to use on house pets such as cats and dogs.

As most insecticidal active ingredients found in cleansing systems such as shampoos are lipophilic, their water solubility is quite limited. To obtain a homogenous and stable product, the active ingredient is generally dispersed in the cleansing system with the aid of surfactants (e.g., wetting agents, emulsifiers, dispersants, and the like). However, formulating such a dispersion is challenging and also requires a high level of surfactants to cover the large surface area. Typically, a clear shampoo usually remains clear upon dilution without the insecticide precipitating out. In addition, most cleansing systems contain one or more "cleaning agents," which are also surfactants capable of removing lipophilic matter such as oils, from hair or skin. In addition, the amount of cleaning agent within the cleansing system is usually a high percentage of the total weight of the formulation. With this large amount of surfactant contained within the cleansing system, a substantial amount of the active ingredient is washed away with the surfactant molecules when rinsed, potentially leading to environmental contamination. This also leads to a short duration of insecticidal activity.

In view of the foregoing, there is a need for a pet cleansing system having longer duration of insecticidal activity. Further, there is a need to enhance the physical stability and aesthetics of a product as well as the uniform coverage of the active ingredient on the hair or skin, and thus it is desirable to disperse the active ingredient into a nanometer sized range within the cleansing system so that the product appears clear and homogeneous. The present invention satisfies these and other needs.

BRIEF SUMMARY OF THE INVENTION

The present invention provides a cleansing system comprising, consisting essentially of, or consisting of, an insecticide having enhanced efficacy, enhanced safety and longer duration of insecticidal activity. In addition, the cleansing system is useful in decreasing the loss of insecticide washed away, as well as the amount of insecticide contacting humans and clothing. Therefore, the present invention allows for a lower amount of insecticide to be administered to control insect infestation than would otherwise be possible using spot-on topical formulations, making it more friendly to the environment.

As such, in one embodiment, the present invention provides an insecticidal cleansing emulsion system (CES) comprising, consisting essentially of, or consisting of, a clear oil-in-water (o/w) emulsion, wherein the oil phase contains an ionic surfactant and an insecticide suspended together as nanometer sized particles in the water phase; and the water phase contains an oppositely charged polymer and optionally a salt. The insecticidal CES appears clear, but upon dilution with water, the ionic surfactant carrying the insecticide forms a water-insoluble complex with the oppositely charged polymer, causing the diluted formulation to turn turbid. The complex carrying the insecticide precipitates out of the water phase and deposits onto the hair or skin.

In certain embodiments, the insecticide is preferably a pyrethroid such as natural pyrethrin or a synthetic pyrethroid. Suitable pyrethroids include pyrethroid esters and pyrethroid ethers. In certain aspects, the insecticidal cleansing emulsion system includes a salt. Suitable salts include alkali metal salts and alkaline earth metal salts.

In another embodiment, the present invention provides a method for preparing an insecticidal cleansing emulsion system, comprising, consisting essentially of, or consisting of, preparing an oil phase having an ionic surfactant and an insecticide; preparing a water phase having an oppositely charged polymer compared to the oil phase; and admixing the oil phase with the water phase to suspend nanometer sized particles, the particles comprising the ionic surfactant and the insecticide.

In still yet another embodiment, the present invention provides a method for eradicating insects on a pet, comprising, consisting essentially of, or consisting of, administering an insecticidal cleansing emulsion system to the pet, wherein the insecticidal cleansing system comprises an oil-in-water (o/w) emulsion, wherein the oil phase contains an ionic surfactant and an insecticide suspended together as nanometer sized particles in the water phase; and the water phase contains an oppositely charged polymer compared to the oil phase, to thereby eradicate insects on the pet.

Without being bound to a particular theory, it is believed that one possible mechanism of action is the deposition of suspended nanometer sized active ingredient particles upon dilution of the emulsion with water (e.g., upon rinsing). In certain aspects, it is believed that a large amount (e.g., greater than 90%) of the applied active ingredient is deposited on the coat and/or skin of the animal, rather than being washed away as occurs in ordinary cleansing systems such as insecticidal shampoos. The foregoing theory is based in-part upon evidence of a precipitate upon application of a rinse water, which precipitate is not seen with certain prior art insecticidal shampoos. The deposition of "nano-sized" particles lends itself to greater contact with pests and hence lower rates of active ingredient are required to achieve similar efficacy than from other systems such as sprays or spot-ons formulations. In certain aspects, the nanosized particles further comprise a synergist.

In yet another embodiment, the present invention provides a method for preparing an insecticidal cleansing emulsion system, comprising, consisting essentially of, or consisting of, preparing an oil phase having an insecticide, an ionic surfactant and optionally a nonionic surfactant serving as a wetting agent; preparing a water phase having an oppositely charged polymer, and optionally a salt foaming agents, pH buffers, rheology agent, and combinations thereof; and admixing the oil phase with the water phase to suspend nanometer sized particles of the oil phase in the water phase.

In still yet another embodiment, the present invention provides a method for eradicating insects on an animal, comprising, consisting essentially of, or consisting of, administering an insecticidal cleansing emulsion system (CES) to the animal, wherein the CES comprises an oil-in-water (o/w) emulsion, wherein the oil phase contains an ionic surfactant and an insecticide suspended together as nanometer sized particles in the water phase; and the water phase contains an oppositely charged polymer and optionally a salt. Upon dilution, a water-insoluble complex of the ionic surfactant carrying the insecticide and the oppositely charged polymer forms a precipitate which deposits onto the pet hair and/or skin.

Other embodiments include the following:
1. An insecticidal cleansing emulsion system, said cleansing emulsion system comprising:
   a clear oil-in-water (o/w) emulsion wherein the oil phase contains an ionic surfactant and an insecticide suspended together as nanometer sized particles in the water phase; and
   wherein said water phase contains an oppositely charged polymer or surfactant and optionally a salt.
2. The insecticidal cleansing emulsion system, wherein said insecticide is a pyrethroid selected from the group consisting of a natural pyrethrin, pyrethroid ester and a pyrethroid ether.
3. The insecticidal cleansing emulsion system, wherein said pyrethroid is a member selected from the group consisting of allethrin, cypermethrin, bifenthrin, cyfluthrin, cyphenothrin, fenpropathrin, deltamethrin, etofenprox, cyhalothrin, permethrin, phenothrin and combinations thereof.
4. The insecticidal cleansing emulsion system, wherein said pyrethroid ether is etofenprox.
5. The insecticidal cleansing emulsion system, wherein said system further comprises an insect growth regulator (IGR).
6. The insecticidal cleansing emulsion system, wherein said IGR is a member selected from the group consisting of methoprene, hydroprene, kinoprene, fenoxycarb, pyriproxifen, and mixtures thereof
7. The insecticidal cleansing emulsion system, wherein said IGR is methoprene.
8. The insecticidal cleansing emulsion system, wherein said ionic surfactant is an anionic surfactant.
9. The insecticidal cleansing emulsion system, wherein said anionic surfactant is a member selected from the group consisting of an alkyl sulfate and an alkyl ether sulfate.
10. The insecticidal cleansing emulsion system, wherein said alkyl sulfate is a member selected from the group consisting of sodium dodecyl sulfate and ammonium lauryl sulfate.
11. The insecticidal cleansing emulsion system, wherein said alkyl ether sulfate is a member selected from the group consisting of sodium laureth sulfate, and ammonium laureth sulfate.
12. The insecticidal cleansing emulsion system, wherein said alkyl ether sulfate is ammonium laureth sulfate.
13. The insecticidal cleansing emulsion system, wherein said oppositely charged polymer is cationic.
14. The insecticidal cleansing emulsion system, wherein said oppositely charged polymer is polyquaternium.
15. The insecticidal cleansing emulsion system, wherein said oppositely charged polymer is polyquaterium-10.
16. The insecticidal cleansing emulsion system, wherein said nanometer sized particles are less than 500 nm.
17. The insecticidal cleansing emulsion system, wherein said nanometer sized particles are less than 100 nm.
18. The insecticidal cleansing emulsion system, wherein said nanometer sized particles are less than 50 nm.
19. The insecticidal cleansing emulsion system, wherein said insecticidal cleansing emulsion system is homogeneous.
20. The insecticidal cleansing emulsion system, wherein said insecticidal cleansing emulsion system further comprises a synergist.
21. The insecticidal cleansing emulsion system, wherein said synergist is a member selected form the group consisting of α-[2-(butoxyethoxy)-ethoxy]-4,5-methylenedioxy-2-propyltoluene (piperonyl butoxide), 1,2-methylenedioxy-4-[2-(octylsulfinyl)propyl]benzene, 4-(3,4-methylenedioxy-phenyl)-5-methyl-1,3-dioxane, and N-(2-ethylhexyl)bicyclo[2,2,1]-hept-5-ene-anhydrophthalic acid-2,3-dicarboxyimide.
22. The insecticidal cleansing emulsion system, wherein said synergist is piperonyl butoxide.
23. The insecticidal cleansing emulsion system, further comprising a salt, wherein said salt is a member selected from the group consisting of an alkali metal salt, an alkaline earth metal salt, an organic salt, a transition metal salt and a combination thereof
24. The insecticidal cleansing emulsion system, wherein said salt is an alkali metal salt.
25. The insecticidal cleansing emulsion system, wherein said alkali metal salt is a member selected from the group consisting of LiCl, NaCl, NaOH, NaOAc, KCl, KOH, KOAc, $Na_2HPO_4$, $NaH_2PO_4$, and $KH_2PO_4$.
26. The insecticidal cleansing emulsion system, further comprising an antioxidant.
27. The insecticidal cleansing emulsion system, wherein said antioxidant is selected from the group consisting of Vitamin E, Vitamin A palmitate, ethoxyquin, propyl gallate, butylated hydroanisole (BHA), butylated hydroxytoluene (BHT), and combinations thereof
28. The insecticidal cleansing emulsion system, wherein said antioxidant is butylated hydroxytoluene (BHT).
29. The insecticidal cleansing emulsion system, further comprising an emollient.
30. The insecticidal cleansing emulsion system, wherein said emollient is a member selected from the group consisting of an ethoxylated lanolin, aloe vera gel and combination thereof
31. The insecticidal cleansing emulsion system, wherein said ionic surfactant and said oppositely charged polymer form a water-insoluble complex.
32. The insecticidal cleansing emulsion system, wherein upon dilution of said emulsion system with water, nanometer sized active ingredient particles precipitate optionally said particles comprise a synergist.
33. A method for eradicating insects on a pet, said method comprising:
   administering an insecticidal cleansing emulsion system to a pet, to eradicate insects on said pet.
34. A method for preparing an insecticidal oil-in water emulsion cleansing system, said method comprising:
   preparing an oil phase having an ionic surfactant and an insecticide;
   preparing a water phase having an oppositely charged polymer and optionally a salt; and
   admixing said oil phase with said water phase to suspend nanometer sized particles of said ionic surfactant with said insecticide in said water phase.
35. The method wherein said insecticide is a pyrethroid selected form the group consisting of a pyrethroid ester and a pyrethroid ether.
36. The method wherein said pyrethroid is a member selected from the group consisting of allethrin, cypermethrin, bifenthrin, cyfluthrin, cyphenothrin, fenpropathrin, deltamethrin, etofenprox, cyhalothrin, permethrin, phenothrin and combinations thereof 37. The method wherein said pyrethroid ether is etofenprox.
38. The method wherein said system further comprises an insect growth regulator (IGR).
39. The method wherein said IGR is a member selected from the group consisting of methoprene, hydroprene, kinoprene, fenoxycarb, pyriproxifen, and mixtures thereof
40. The method wherein said IGR is methoprene.
41. The method wherein said ionic surfactant is an anionic surfactant.
42. The method wherein said anionic surfactant is a member selected from the group consisting of alkyl sulfates and alkyl ether sulfates.
43. The method wherein said alkyl sulfate is a member selected from the group consisting of sodium dodecyl sulfate and ammonium lauryl sulfate.
44. The method wherein said alkyl ether sulfate is a member selected from the group consisting of sodium laureth sulfate and ammonium laureth sulfate.
45. The method wherein said alkyl ether sulfate is ammonium laureth sulfate.
46. The method wherein said oppositely charged polymer is cationic.
47. The method wherein said oppositely charged polymer is polyquaternium.
48. The method wherein said oppositely charged polymer is polyquaternium-10.
49. The method wherein said nanometer sized particles are less than 500 nm.
50. The method wherein said nanometer sized particles are less than 100 nm.
51. The method wherein said nanometer sized particles are less than 50 nm.
52. The method wherein said system is homogeneous and clear.
53. The method wherein said insecticidal cleansing emulsion system further comprises a synergist.
54. The method wherein said synergist is a member selected from the group consisting of α-[2-(butoxy-ethoxy)-ethoxy]-4,5-methylene-dioxy-2-propyltoluene (piperonyl butoxide), 1,2-methylenedioxy-4-[2-(octyl-sulfinyl)propyl]benzene, 4-(3,4-methylenedioxy-phenyl)-5-methyl-1,3-dioxane, and N-(2-ethylhexyl)bicyclo[2,2,1]-hept-5-ene-anhydro-phthalic acid-2,3-dicarboxyimide.
55. The method wherein said synergist is piperonyl butoxide.
56. The method further comprising an antioxidant.
57. The method wherein said antioxidant is selected from the group consisting of Vitamin E, Vitamin A palmitate, ethoxyquin, propyl gallate, butylated hydroanisole (BHA), butylated hydroxytoluene (BHT), and combinations thereof.
58. The method wherein said antioxidant is butylated hydroxytoluene (BHT).
59. The method further comprising a salt.
60. The method further comprising an emollient.
61. The method wherein said emollient is a member selected from the group consisting of an ethoxylated lanolin, aloe vera gel and combination thereof.

These and other objects, embodiments and advantages will become more apparent when read with the drawing and detailed description which follow.

DETAILED DESCRIPTION OF THE INVENTION

I. General

Figure 1:
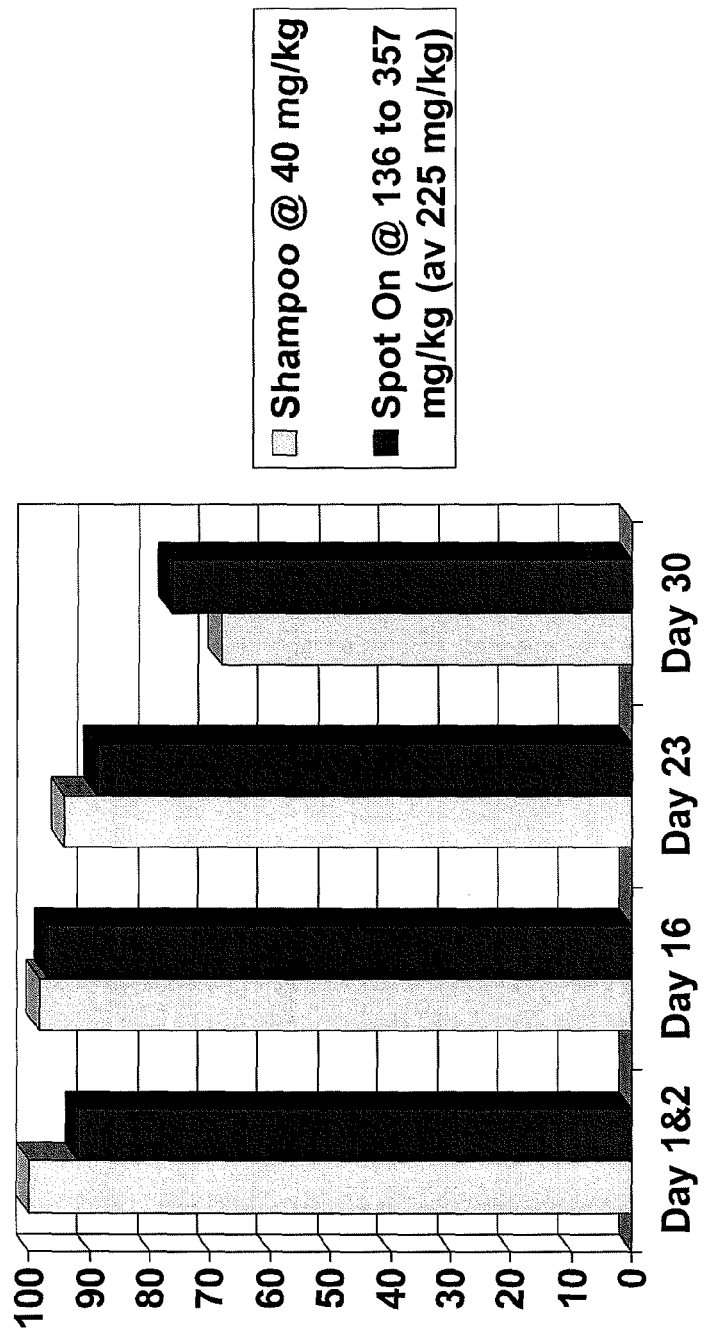
FIG. 1 is a bar graph indicating efficacy of a cleansing emulsion system at 40 mg/kg of the present invention compared to a spot-on formulation 225 mg/kg.

The present invention provides an insecticidal cleansing emulsion system comprising, consisting essentially of, or consisting of, a clear oil-in-water (o/w) emulsion wherein the oil phase contains an ionic surfactant and an insecticide suspended together as nanometer sized particles in the water phase; and the water phase contains an oppositely charged polymer and optionally a salt. As used herein the phrase "cleansing emulsion system" includes a composition such as a shampoo that is applied to the hair or coat of an animal e.g., by scrubbing in the presence of added water, for use in eliminating insects (e.g., fleas, ticks), delousing, disinfecting, cleansing, conditioning, and moisturizing the hair or coat. In certain preferred aspects, the cleansing emulsion system is homogeneous and clear.

In general, a nanometer dispersion is desired for superior physical stability and esthetics of the product. However, such a dispersion may impact the amount of insecticidal active ingredient being deposited. Advantageously, the present invention provides a high level of active ingredient being deposited while still maintaining a superior physical stability of the formulation. In certain instances, the homogeneity of the product is disrupted to allow the active ingredient to separate from the water phase and precipitate on the hair of the animal, instead of being washed away with the rinsate.

In certain preferred aspects, the present invention provides an ionic surfactant in the oil phase which tends to maximize the association of a water-insoluble insecticide with the hydrophobic portion of an ionic surfactant. In addition, the water phase comprises, consists essentially of, or consists of, an oppositely charged polymer compared to the ionic surfactant present in the oil phase. For example, if the oil phase contains an anionic surfactant, the water phase contains a cationic polymer (e.g., cationic surfactant) and visa versa. Upon dilution, the oppositely charged polymer forms a water insoluble complex with the ionic surfactant of the oil phase. The percentage of the ionic surfactant and the oppositely charged polymer in the cleaning system is chosen at a level that a water insoluble complex forms. In certain preferred aspects, a salt is added to prevent the formation of a water insoluble complex between the ionic surfactant and the oppositely charged polymer within the cleaning system, so that a homogenous and clear composition is more stable. During the rinsing process or alternatively, when the product is diluted, the ionic surfactant carrying the insecticide and the oppositely charged polymer forms a water insoluble complex which precipitates out and is deposited onto the hair or skin of the animal.

II. Topical Formulations

A. Active Ingredient

The cleansing emulsion system of the present invention contains one or more insecticides. The insecticide is effective to kill fleas, flea eggs, flea larvae, ticks, tick larvae, tick nymphs and lice. In certain other instances, the insecticide kills head lice, adult lice, nits and eggs. The selection of the insecticide component produces an insecticide having high insecticidal activity with long duration and increased efficacy.

In a preferred embodiment, the insecticide of the present invention is a pyrethroid such as pyrethrin or a synthetic pyrethroid. Additional pyrethroids or non-pyrethroid insecticides can also be used. Preferably, the pyrethroid can be a pyrethroid ester and/or a pyrethroid ether. Pyrethroid esters include for example, acrinathrin, bifenthrin, cyhalothrin, cypermethrin, alpha-cypermethrin, fenpropathrin, fenvalerate, flucythrinate, flumethrin, fluvalinate, tau-fluvalinate, permethrin and combinations thereof. Pyrethroid ethers include for example, etofenprox and halfenprox. Preferred pyrethroids include, but are not limited to, allethrin, cypermethrin, bifenthrin, cyfluthrin, deltamethrin, etofenprox, cyhalothrin, permethrin, phenothrin and combinations thereof. Others include cyphenothrin and/or fenpropathrin. In an especially preferred embodiment the pyrethroid ether is etofenprox.

In certain embodiments, the cleansing emulsion system further includes an insect growth regulator (IGR). Suitable IGRs include, but are not limited to, chitin synthesis inhibitors such as bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, and triflumuron. In addition, juvenile hormone mimics are suitable such as epofenonane, fenoxycarb, hydroprene, kinoprene, methoprene, pyriproxyfen, and triprene. Further, juvenile hormones are suitable such as juvenile hormone I, juvenile hormone II, and juvenile hormone III. Other suitable IGRs include, molting hormone agonists, chromafenozide, halofenozide, methoxyfenozide and tebufenozide. Moreover, molting hormones such as α-ecdysone, and ecdysterone are suitable. In addition, molting inhibitors such as diofenolan and other IGRs, which include precocenes, such as precocene I, precocene II, and precocene III are suitable. Finally, unclassified insect growth regulators are suitable such as dicyclanil. Preferred IGRs include methoprene, hydroprene, kinoprene, fenoxycarb, pyriproxifen, and mixtures thereof. In the most preferred embodiment, methoprene is the IGR of choice. As used herein, "methoprene" includes R-methoprene, S-methoprene and mixtures of R and S methoprene at all percentages of either isomer. S-methoprene is the preferred methoprene.

The amount of active ingredient can vary with the desired application and insect to be eradicated. In one embodiment of the invention, the insecticide is a synthetic pyrethroid. In a preferred embodiment of the invention, the pyrethroid ether (e.g., etofenprox) is dissolved in the formulation to a concentration range of about 0.005 to 15% w/w, preferably about 0.05 to 5% w/w, more preferably about 0.1% to 3% w/w and most preferably, about 0.2% to 1.1% w/w. In another preferred embodiment of the invention, the formulation comprises, consists essentially of, or consists of, a dosage of at least about 8 g/kg to an animal. Therefore, in certain instances, the formulation contains 0.5% w/w, which is an acceptable insecticide dosage for an average cat of about 40 mg/kg.

In certain aspects, the cleansing emulsion system of the present invention further comprise a synergist. A preferred synergist is piperonyl butoxide (PBO). Other suitable synergists include, but are not limited to, α-[2-(butoxyethoxy)-ethoxy]-4,5-methylene-dioxy-2-propyltoluene (hereinafter referred to as PBO), 1,2-methylenedioxy-4-[2-(octylsulfinyl) propyl]benzene (hereinafter referred to as sulfoxide), 4-(3,4-methylenedioxy-phenyl)-5-methyl-1,3-dioxane (hereinafter referred to as safroxane), etc. There are other kinds of synergist on the market including N-(2-ethylhexyl)bicyclo[2,2,1]-hept-5-ene-anhydro-phthalic acid-2,3-dicarboxyimide (trade mark: MGK-264, McLaughlin Gormley King Co.), and the like. U.S. Pat. No. 3,970,703 incorporated herein by reference, discloses other synergists useful in the present invention.

In certain instances, piperonyl butoxide has prominent synergistic effect on natural pyrethrin. MGK-264 has excellent synergistic effect on allethrin. Those of skill in the art will know if other synergists suitable for use in the present invention. In general, the amount of synergist in the formulation depends of the active ingredient used. The amount of synergist can vary between 0.1% to about 5% w/w. In certain instances, the amount of synergist is preferably about 0.5% to 2.5% w/w. In certain instances, the ratio of synergist to active ingredient is about 0.5:2 to about 2:0.5, preferably about 0.5:1.5 to about 1.5:0.5.

B. Surfactants

In certain embodiments, the oil phase of the present invention contains a surfactant (e.g., surface-active agents), i.e., an emulsifying agent, such as a cationic, an anionic and/or a nonionic emulsifying agent e.g., polyethylene oxide esters of fatty acids, polyethylene oxide ethers of fatty alcohols, alkyl sulfates, alkyl sulfonates, aryl sulfonates, albumin hydrolyzates, alkyl arylpolyglycol ethers, magnesium stearate, sodium oleate, and/or dispersing agents such as methyl cellulose, and the like.

In certain preferred embodiments, the oil phase contains an ionic surfactant such as for example, an anionic surfactant. Suitable anionic surfactants include, but are not limited to, sodium laureth sulfate, sodium dodecyl sulfate, ammonium lauryl sulfate and combinations thereof. In a preferred embodiment, the anionic surfactant is ammonium lauryl sulfate. Addition examples of the anionic surfactants, include sodium aryl sulfate, sodium mono- or di-alkylnapthalenesulfonates, sodium alpha-oleinsulfonate, sodium alkanesulfonate, alkyl sulfates, polyoxyalkylene alkyl ether sulfonates, polyoxyalkylene alkylaryl ether sulfates, polyoxyalkylene styrylphenyl ether sulfates, mono- or di-alkylbenzenesulfonates, alkylnapthalenesulfonates, alkyl-naphthalenesulfonate/formaldehyde condensates, alkyl diphenyl ether sulfonates, olefinic sulfonates. alkyl phosphates, polyoxyalkylene alkyl phosphates, polyoxyalkylene phenyl ether phosphates, polyoxyalkylphenol phosphates, polycarboxylic acid salts, fatty acid salts, stearic acid and its salts, oleic acid and its salts, N-methyl fatty acid taurides and mixtures consisting of two or more compounds selected from among those cited above, involving sodium, potassium, ammonium and amine salts.

In certain aspects, the oil phase optionally comprises a non-ionic surfactant. Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, polyoxyalkylene block copolymer alkylglycerol esters, polyoxyalkylene alkyl sulfonamides, polyoxyalkylene rosin esters, polyoxypropylene block copolymers, polyoxyethylene oleyl ethers, polyoxyalkylene alkylphenols and mixtures consisting of two or more of these substances.

In one embodiment of the invention, the concentration range of surfactant is about 1% to 30% w/w, more preferably about 5% to 25% w/w, and most preferably about 10% to 20% w/w.

In certain aspects, the present formulation provides surfactant micelles such as micro-sized or nano-sized micelle particles, wherein the active ingredient is encapsulated within the surfactant micelle particle. In certain aspects, the nanometer sized particles are less than 500 nm. Preferably, the nanometer sized particles are less than 100 nm. In a more preferred embodiment, the nanometer sized particles are less than 50 nm.

C. Emulsion

In certain aspects, the present invention provides a clear emulsion or microemulsion, wherein the dispersed phase (e.g., oil) contains an ionic surfactant (e.g., an anionic surfactant) and an insecticide suspended as nanometer sized particles in the continuous phase (e.g., water). The oil is immiscible in water and thus, is dispersed as liquid droplets through the continuous phase, usually but not necessarily water. In certain preferred aspects, the emulsion is clear allowing visible light to penetrate through the formulation. This is an indication that any suspended particles are in the nanometer size range which is less than the wavelength of visible light.

In certain aspects, the continuous phase (e.g., water) components make up to 60% by weight of the total composition, preferably up to 65% by weight of the composition and more preferably up to 70% of the composition. The continuous phase (e.g., water) comprises an oppositely charged polymer (e.g., surfactant) compared to the dispersed phase. For example, if the dispersed phase comprises an anionic surfactant, the continuous phase contains a cationic polymer and visa versa. In certain aspects, the continuous phase components make up to 75%, up to 80%, up to 85% or higher. In certain instances, the continuous phase components make up to 90% of the total weight of the composition.

The water phase contains an oppositely charged polymer compared to the oil phase. For example, if the oil phase contains an anionic surfactant, the water phase contains a cationic polymer. If the oil phase comprises a cationic surfactant, the water phase will comprise an anionic polymer or surfactant.

In one aspect, the oil phase contains an anionic surfactant and therefore the water phase contains a cationic polymer. One preferred cationic polymer is a polyquaternium such as Polyquaternium-10. Other suitable examples of the cationic polymers or surfactants include alkylamines, alkyl imidazolines, ethoxylated amines, gelatin and chitosan, e.g., alkylbenzyldimenthylammonium salts, alkylbetaines, heterocyclic ammonium salts, tetraalkylammonium salts, ethoxylated tallow amine, ethoxylated oleylamine, ethoxylated soy amine, ethoxylated coco amine, ethoxylated synthetic alkylamine and ethoxylated octylamine and mixtures consisting of two or more of these substances.

D. Salt

In certain preferred embodiments, the emulsion herein comprises at least one salt. Suitable salts include an alkali metal salt, an alkaline earth metal salt, an organic salt, a transition metal salt and a combination thereof. Alkali metals are the elements comprising Group 1 of the periodic table: lithium (Li), sodium (Na), potassium (K), rubidium (Rb), caesium (Cs), and francium (Fr). Suitable salts include LiCl, NaCl, NaOH, NaOAc, KCl, KOH, KOAc, $Na_2HPO_4$, $NaH_2PO_4$, $KH_2PO_4$, and the like. The alkaline earth metals comprise Group 2 of the periodic table: beryllium (Be), magnesium (Mg), calcium (Ca), strontium (Sr), barium (Ba) and radium (Ra). Suitable salts include, $CaCl_2$, $CaOH_2$, $MgCl_2$, $MgSO_4$, and the like. Other salts include, Tris(hydroxymethyl)aminomethane hydrochloride (Tris-HCl), succinic acid (disodium salt), Tris-acetate, Citric acid (Trisodium), and a combination thereof.

In certain embodiments, the insecticidal cleansing emulsion system of the present invention contains about 0.001% w/w to about 15% w/w of a suitable salt. Preferably, the cleansing system of the present invention contains about 0.01% to about 10% w/w. In one aspect, the cleansing system contains about 0.1%, 0.2%, 0.3%, 0.4%, 0.5%, 0.6%, 0.7%, 0.8%, 0.9%, or 1.0% w/w salt. In another aspect, the cleansing system contains about 1%, 2%, 3%, 4%, 5%, 6%, 7%, 8%, 9%, or 10% w/w salt.

Without being bound by any particular theory, it is believed that the presence of a salt in the cleansing emulsion allows for more efficient release of the active ingredient (e.g., >90%) onto the coat of an animal (e.g., short hair, long hair and the like) when water is introduced and the cleansing system emulsion is diluted. It is believed that the salt facilitates the ionic surfactant carrying the insecticide to form a water-insoluble complex with the oppositely charged polymer when water is introduced. This complex precipitates out of the water phase and deposits onto the hair or skin.

III. Methods of Making

In certain embodiments, the present invention provides a method for preparing an insecticidal oil-in-water emulsion cleansing system, comprising: preparing an oil phase having an ionic surfactant and an insecticide; preparing a water phase having an oppositely charged polymer compared to the oil phase; and admixing the oil phase with the water phase to suspend nanometer sized particles of the ionic surfactant with the insecticide in the water phase. In certain embodiments, the water phase has a salt included therein.

Other additives to the insecticidal composition include, but are not limited to, fragrances, surfactants and spreading agents, which can increase performance such as polysorbate 20 and polysorbate 80, and isopropyl myristate. Polymers such as agar, gelatin, alginate, and cationic polymers such as cationic agar, cationic cellulose, cationic acrylates, and polyoxymethylene urea may also be added to improve safety and adhesion to skin and hair.

It will be readily appreciated by the skilled artisan that the formulations described herein may also comprise additives including, but not limited to, fragrances, hair conditioners, solvation aids, spreading agents, solubilizers and UV protectants.

In certain aspects, the formulations of the present invention further comprise an antioxidant. Suitable antioxidants include, but are not limited to, Vitamin E, Vitamin E acetate, Vitamin A palmitate, propyl gallate, butylated hydroxyanisole (BHA), butylated hydroxytoluene (BHT), and combinations thereof.

In still other aspects, the insecticidal cleansing emulsion system of the present invention further comprises an emollient. Suitable emollients include, but are not limited to, an ethoxylated lanolin, aloe vera gel and combination thereof.

IV. Uses

In practice, an effective amount of the insecticidal compositions as described herein may be applied to a companion animal, preferably a cat or a dog, as a foaming cleansing system, dip, aerosol spray, pump spray, powder, lotion, emulsifiable concentrate, aqueous or liquid flowable, suspension concentrate and by any other methods suitable for administering topical compositions to animals.

The formulation according to the invention is particularly preferably administered to companion animals such as cats and dogs, but can be suitable for other mammals, such as horses, gerbils, hamsters, mice, reptiles and other household or domesticated animals.

When used on cats, approximately 150-200 mg of the insecticide may be administered to a cat weighing less than 5 kilograms and up to 300-350 mg may be administered to a cat weighing 5 kilograms or more. Preferably, the amount of the insecticide being administered to a cat is about 200 mg for a cat weighing less than 5 kilograms and between about 250-300 mg for a cat weighing 5 kilograms or more. An amount of approximately 8-10 g of product per kg body weight for an etofenprox containing product is preferred.

When used on dogs, preferably, approximately up to 600-650 mg may be administered to a dog weighing under 15 kilograms, approximately up to 880-900 mg of total insecticide may be administered to a dog weighing less than 22 kilograms, approximately up to 1.2 grams of total insecticide may be administered to a dog weighing 20-30 kilograms, approximately up to 1.8 grams of total insecticide may be administered to a dog weighing 30-45 kilograms, and approximately up to 2.0-2.5 gm of total insecticide may be administered to a dog weighing over 45 kilograms. Preferably, the amount of etofenprox in the composition is between 280-300 mg for a dog weighing 2 to 7 kilograms, between about 600-650 mg for a dog weighing 8 to 15 kilograms, between about 800-850 mg for a dog weighing 15-20 kilograms, between about 1,200-1250 mg for a dog weighing 20 to 30 kilograms, between about 1,800-1850 mg for a dog weighing 30 to 45 kilograms, and between about 2,000-2100 mg for a dog weighing more than 45 kilograms. An amount of approximately 8-10 g of product per kg body weight for an etofenprox containing product is preferred.

In certain aspects, the preparations are suitable for combating insect infestations which occur in animal husbandry and animal breeding in productive, breeding, zoo, laboratory, experimental animals and pets, and have a favorable toxicity to warm-blooded animals. Production and breeding animals include mammals, such as, for example, cattle, horses, sheep, pigs, goats, camels, water buffalo, donkeys, rabbits, fallow deer and reindeer, and pelt animals, such as, for example, mink, chinchilla and raccoons. Laboratory and experimental animals include mice, rats, guinea pigs, hamsters, dogs and cats.

In certain aspects, the preparations are suitable for combating insect infestations which occur in animal husbandry and animal breeding in production breeding, zoo, laboratory, experimental animals and pets, and have a favorable toxicity to warm-blooded animals. Production and breeding animals include mammals, such as, for example, cattle, horses, sheep, pigs, goats, camels, water buffalo, donkeys, rabbits, fallow deer and reindeer, and pelt animals, such as, for example, mink, chinchilla and raccoons. Laboratory and experimental animals include mice, rats, guinea pigs, hamsters, dogs and cats.

V. Examples

Example 1 illustrates a cleansing emulsion system formulation having enhanced residual flea efficacy.

Formulation 1 is illustrated in Table 1A.

TABLE 1A

Pet cleansing emulsion system formulation

| Ingredient Name | Description | % W/W |
|---|---|---|
| 1) ETO (98.5%) | Etofenprox | 0.510% |
| 2) PBO (87.67%) | Piperonyl Butoxide | 1.710% |
| 3) Tween 20 | Polysorbate 20 | 6.00% |
| 4) Steol CA-460 | Ammonium Laureth Sulfate | 13.00% |
| 5) Ucare JR-30M | Poly uaternium-10 | 0.40% |
| 6) Amphosol CA | Cocamidopropyl Betaine | 25.00% |

TABLE 1A-continued

Pet cleansing emulsion system formulation

| Ingredient Name | Description | % W/W |
|---|---|---|
| 7) Dionized Water | Carrier | 50.27% |
| 8) Other | Fragrance, colorant, preservative, etc | 3.11% |
| Total | | 100.00% |

Formulation 2 is shown in Table 1B. Formulation 2 comprises a salt.

TABLE 1B

Pet cleansing emulsion system formulation

| Ingredient Name | Description | % W/W |
|---|---|---|
| 1) ETO (98.5%) | Etofenprox | 0.510% |
| 2) PBO (87.67%) | Piperonyl Butoxide | 1.710% |
| 3) Tween 20 | Polysorbate 20 | 6.00% |
| 4) Steol CA-460 | Ammonium Laureth Sulfate | 13.00% |
| 5) Ucare JR-30M | Polyquaternium-10 | 1.00% |
| 6) Amphosol CA | Cocamidopropyl Betaine | 20.00% |
| 7) NaCl | Sodium Chloride | 0.50% |
| 8) Dionized Water | Carrier | 55.78% |
| 9) Other | Fragrance, colorant, preservative, etc | 1.50% |
| Total | | 100.00% |

Example 2 illustrates a cleansing emulsion system having enhanced residual flea efficacy.

Etofenprox is an insecticide with low mammalian toxicity and high insecticidal properties. In general, topical formulations usually show relatively good initial kill of fleas, but require high rates for extended residual efficacy on cats (see Tables 2-4).

TABLE 2

Study A ETO Spot On 40% ETO + 3.6% S-Methoprene

| Animal ID | Animal Wt (kg.) | Vol Dosed (ml) | Dose Rate (mg/kg) | Day 2 Number of Fleas | Day 16 Number of Fleas | Day 23 Number of Fleas | Day 30 Number of Fleas |
|---|---|---|---|---|---|---|---|
| Group 1: Untreated (Negative) Controls | | | | | | | |
| 1 | N/A | 0 | 0 | 57 | 75 | 67 | 62 |
| 2 | N/A | 0 | 0 | 53 | 61 | 84 | 78 |
| 3 | N/A | 0 | 0 | 65 | 62 | 81 | 76 |
| Geometric Mean | | | | 58.12 | 65.70 | 76.96 | 71.63 |
| Group 2: 40% ETO + 3.6% (S)-Methoprene | | | | | | | |
| 4 | 4.12 | 2 | 194.17 | 0 | 0 | 4 | 8 |
| 5 | 2.62 | 2 | 305.34 | 4 | 1 | 5 | 32 |
| 6 | 2.66 | 2 | 300.75 | 5 | 4 | 12 | 37 |
| Geometric Mean | | | | 2.11 | 1.15 | 6.21 | 21.16 |
| % Reduction | | | | 96.37 | 98.24 | 91.93 | 70.46 |

TABLE 3

Study B ETO Spot On 40% ETO + 3.6% S-Methoprene

| Animal ID | Animal Wt (kg.) | Vol Dosed (ml) | Dose Rate (mg/kg) | Day 2 Number of Fleas | Day 16 Number of Fleas | Day 23 Number of Fleas |
|---|---|---|---|---|---|---|
| Group 1: Untreated (Negative) Controls | | | | | | |
| 1B | 5.44 | 0 | 0 | 89 | 68 | 77 |
| 2B | 4.14 | 0 | 0 | 68 | 51 | 81 |
| 3B | 2.76 | 0 | 0 | 62 | 56 | 68 |

TABLE 3-continued

Study B ETO Spot On 40% ETO + 3.6% S-Methoprene

| Animal ID | Animal Wt (kg.) | Vol Dosed (ml) | Dose Rate (mg/kg) | Day 2 Number of Fleas | Day 16 Number of Fleas | Day 23 Number of Fleas |
|---|---|---|---|---|---|---|
| 4B | 2.27 | 0 | 0 | 66 | 60 | 75 |
| 5B | 2.25 | 0 | 0 | 66 | 78 | 76 |
| 6B | 1.84 | 0 | 0 | 64 | 73 | 72 |
| | | | Geometric Mean | 68.64 | 63.63 | 74.72 |
| Group 2: 40% ETO + 3.6% (S)-Methoprene | | | | | | |
| 7B | 5.14 | 2 | 155.64 | 13 | 11 | 31 |
| 8B | 4.28 | 2 | 186.92 | 1 | 5 | 30 |
| 9B | 4.26 | 2 | 187.79 | 1 | 6 | 28 |
| 10B | 3.53 | 2 | 226.63 | 3 | 3 | 16 |
| 11B | 2.92 | 2 | 273.97 | 11 | 1 | 0 |
| 12B | 2.12 | 1 | 188.68 | 9 | 5 | 38 |
| 13B | 2.19 | 1 | 182.65 | 2 | 7 | 36 |
| 14B | 2.18 | 1 | 183.49 | 6 | 35 | 46 |
| 15B | 2.04 | 1 | 196.08 | 12 | 12 | 42 |
| 16B | 1.74 | 1 | 229.89 | 3 | 33 | 56 |
| | | | Geometric Mean | 4.19 | 7.38 | 23.93 |
| | | | % Reduction | 93.90 | 88.40 | 67.97 |

TABLE 4

Study C ETO Spot On 40% ETO + 3.6% S-Methoprene

| Animal ID | Animal Wt (kg.) | Vol Dosed (ml) | Dose Rate (mg/kg) | Day 2 Number of Fleas | Day 16 Number of Fleas | Day 23 Number of Fleas | Day 30 Number of Fleas |
|---|---|---|---|---|---|---|---|
| Group 1: Untreated (Negative) Controls | | | | | | | |
| 1C | 6.49 | 0 | 0 | 56 | 71 | 81 | 74 |
| 2C | 5.48 | 0 | 0 | 61 | 79 | 106 | 93 |
| 3C | 4.50 | 0 | 0 | 60 | 68 | 81 | 67 |
| 4C | 3.31 | 0 | 0 | 70 | 57 | 70 | 89 |
| 5C | 1.45 | 0 | 0 | 63 | 74 | 103 | 124 |
| 6C | 1.29 | 0 | 0 | 68 | 65 | 60 | 60 |
| | | | Geometric Mean | 62.8 | 68.6 | 81.9 | 82.1 |
| Group 2: 40% ETO + 3.6% (S)-Methoprene | | | | | | | |
| 7C | 5.87 | 2 | 136.29 | 9 | 0 | 4 | 4 |
| 8C | 5.29 | 2 | 151.23 | 35 | 1 | 3 | 18 |
| 9C | 4.93 | 2 | 162.27 | 12 | 4 | 8 | 13 |
| 10C | 4.60 | 2 | 173.91 | 10 | 1 | 18 | 54 |
| 11C | 4.81 | 2 | 166.32 | 2 | 7 | 32 | 60 |
| 12C | 3.20 | 2 | 250.00 | 4 | 0 | 11 | 19 |
| 13C | 3.15 | 2 | 253.97 | 4 | 1 | 8 | 28 |
| 14C | 2.74 | 2 | 291.97 | 3 | 0 | 2 | 1 |
| 15C | 1.28 | 1 | 312.50 | 3 | 7 | 15 | 70 |
| 16C | 1.12 | 1 | 357.14 | 1 | 19 | 23 | 61 |
| | | | Geometric Mean | 5.1 | 2.0 | 9.0 | 19.2 |
| | | | % Reduction | 92.0 | 97.1 | 89.0 | 76.6 |

Etofenprox at relatively low rates, (40 mg/kg BW, table 5) produced residual efficacy results similar to 225 mg/kg BW rates required for topical formulations.

TABLE 5

Study D ETO cleansing emulsion system: RF2057; 0.5% ETO &1.5% PBO

| Animal ID | Animal Wt (kg) | Target Wt. of Dose (g) | Dose Rate (mg/kg) | Day 1 Number of Fleas | Day 4 Number of Fleas | Day 9 Number of Fleas | Day 16 Number of Fleas | Day 24 Number of Fleas | Day 30 Number of Fleas |
|---|---|---|---|---|---|---|---|---|---|
| Group 1: Untreated (Negative) Controls | | | | | | | | | |
| 1D | 5.39 | 0 | 0 | 56 | 61 | 73 | 75 | 62 | 55 |
| 2D | 4.69 | 0 | 0 | 43 | 63 | 47 | 63 | 80 | 63 |
| 3D | 4.45 | 0 | 0 | 49 | 76 | 60 | 63 | 63 | 51 |
| | | | Geometric Mean | 49.0 | 66.3 | 59.0 | 66.8 | 67.9 | 56.1 |
| Group 2: 0.5% ETO, 1.5% PBO | | | | | | | | | |
| 4D | 6.45 | 51.60 | 40.00 | 0 | 0 | 3 | 0 | 1 | 16 |
| 5D | 4.85 | 38.80 | 40.00 | 0 | 0 | 0 | 1 | 3 | 12 |
| 6D | 3.76 | 30.08 | 40.00 | 0 | 3 | 3 | 3 | 13 | 29 |
| | | | Geometric Mean | 0.0 | 0.6 | 1.5 | 1.0 | 3.8 | 17.8 |
| | | | % Reduction | 100.0 | 99.1 | 97.4 | 98.5 | 94.4 | 68.3 |

The efficacy trials were performed using protocols that required the experimental group of infested cats to be compared with an untreated group of similarly infested animals.

The cleansing emulsion system formulation, containing 0.5% etofenprox was applied to the wet animals at the rate of 8 grams of cleansing system per kg of animal body weight. The 40% etofenprox topical was applied at the rate of 1 ml per cat for weights up to 5 lbs. (2.2 kg) and 2 ml per cat for those weighing greater than 5 lbs. (2.2 kg). The average rate of etofenprox applied to the cleansing system treated cats was 40 mg etofenprox per kg of body weight. The average rate of etofenprox applied to the topical treated cats was 225 mg per kg of body weight.

All test animals were infested with 100 unfed adult cat fleas prior to treatment. The cats were examined for the presence of live fleas at 24 to 48 hours after treatment. Residual data points were accomplished by infesting the treated animals at 14, 21 and 28 days after treatment. The animals were then examined for the presence of live fleas 48 hours after each infestation.

Results are presented in FIG. 1. Similar residual adult flea kill was obtained using the cleansing system at 40 mg/kg A.I. (Table 5) as were obtained with the Topical at an average rate of 225 mg/kg. A.I. (Table I). In certain instances, the on-animal retention of etofenprox after rinsing was about 24 mg/kg body weight.

Example II

This Example illustrates the amount of synergist and active ingredient remained on cat after rinsing.

TABLE 6

ETOFENPROX INSECTICIDAL
CLEANSING SYSTEM RINSE WATER RESULTS

| CAT | % PBO * REMAINED ON CAT | % ETOFENPROX * REMAINED ON CAT |
|---|---|---|
| ETO Formula with Salt (Table 1B) | | |
| ALFALFA | 85.90% | 100.00% |
| VICTORIA | 89.92% | 99.92% |
| NITO | 91.59% | 97.86% |
| ZEUS | 90.38% | 94.36% |
| ETO Formula without salt (Table 1A) | | |
| KAREN | 80.42% | 83.27% |
| RICHARD | 55.88% | 59.64% |
| KIM | 65.41% | 71.11% |
| MALCOLM | 45.87% | 48.06% |

*These values are derived from the amount of active ingredient put on the cat and the amount of active ingredient found in the rinse solution.

Figure 2:
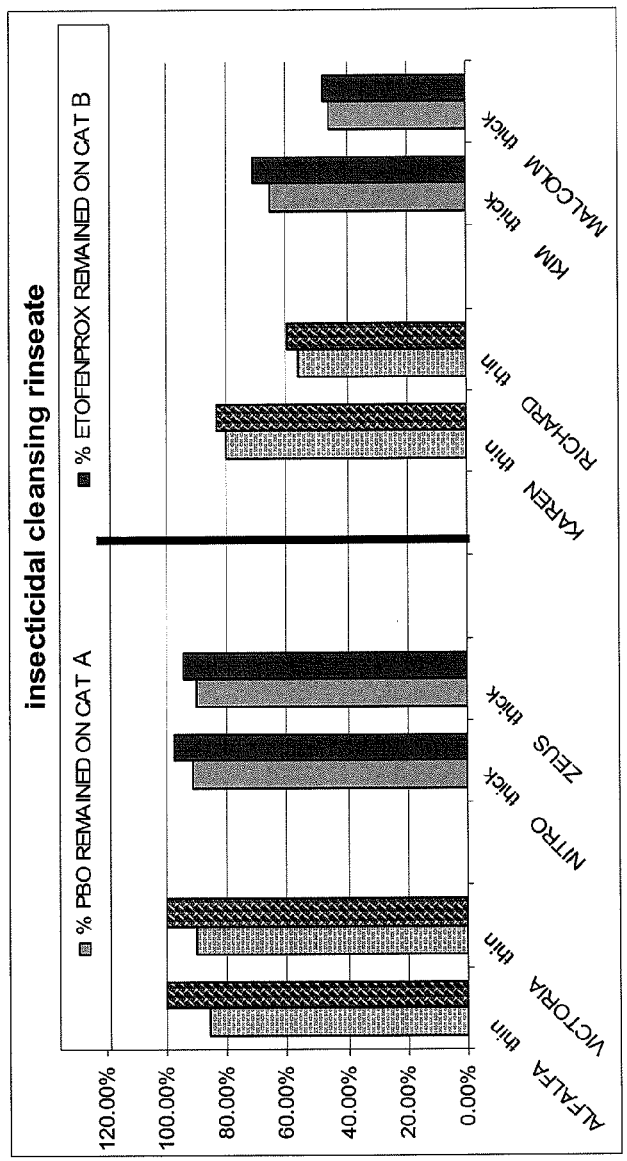
FIG. 2 A-B shows a bar graph and the amount of synergist remaining on the cat FIG. 2A; and the amount of etofenprox remaining on the cat FIG. 2B.

FIGS. 2A and B illustrate the tabulated data.
Comparative

Table 7 is data for comparative formulations, which illustrates the amount of active ingredient that stays on the animal's fur. Comparing the data for the inventive formulations shown in Table 6 and for the comparative formulations shown in Table 7, it is evident that the inventive formulation is superior in the amount of residual active on the animals' fur.

TABLE 7

| Comparative Formulation 1 | w/w % | g in sample | % Stayed on Cat |
|---|---|---|---|
| PBO | 1.5 | 0.697 | 67 |
| Total Pyrethrin | 0.1500 | 0.0697 | 79 |
| Comparative Formulation 2 | w/w % | g in sample | % Stayed on Cat |
| Total MGK264 | 0.151 | 0.0653 | 76 |
| Bioallethrin | 0.109 | 0.0471 | 58 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An insecticidal cleansing emulsion system, said cleansing emulsion system comprising:
   a clear oil-in-water (o/w) emulsion wherein the oil phase contains an ionic surfactant, wherein the ionic surfactant is an anionic surfactant and wherein the anionic surfactant is a member selected from the group consisting of an alkyl sulfate and an alkyl ether sulfate; and
   an insecticide suspended as nanometer sized particles in the water phase; and wherein said water phase contains a cationic polymer or surfactant, and a metal salt selected from the group consisting of LiCl, NaCl, $CaCl_2$, $MgCl_2$, $MgSO_4$, NaOAc, KCl, KOH, KOAc, $Na_2HPO_4$, and $NaH_2PO_4$; wherein upon dilution with water, said anionic surfactant and said cationic polymer or surfactant form a water-insoluble complex and said nanometer sized insecticide particles precipitate out of the water phase together with the water-insoluble complex.

2. The insecticidal cleansing emulsion system of claim 1, wherein said insecticide is a pyrethroid selected from the group consisting of a natural pyrethrin, pyrethroid ester and a pyrethroid ether.

3. The insecticidal cleansing emulsion system of claim 2, wherein said pyrethroid is a member selected from the group consisting of allethrin, cypermethrin, bifenthrin, cyfluthrin, cyphenothrin, fenpropathrin, deltamethrin, etofenprox, cyhalothrin, permethrin, phenothrin and combinations thereof.

4. The insecticidal cleansing emulsion system of claim 3, wherein said pyrethroid ether is etofenprox.

5. The insecticidal cleansing emulsion system of claim 1, wherein said system further comprises an insect growth regulator (IGR).

6. The insecticidal cleansing emulsion system of claim 5, wherein said IGR is methoprene.

7. The insecticidal cleansing emulsion system of claim 1, wherein said alkyl sulfate is a member selected from the group consisting of sodium dodecyl sulfate and ammonium lauryl sulfate.

8. The insecticidal cleansing emulsion system of claim 1, wherein said alkyl ether sulfate is a member selected from the group consisting of sodium laureth sulfate, and ammonium laureth sulfate.

9. The insecticidal cleansing emulsion system of claim 1, wherein said cationic polymer is polyquaternium.

10. The insecticidal cleansing emulsion system of claim 1, wherein said nanometer sized particles are less than 500 nm.

11. The insecticidal cleansing emulsion system of claim 1, wherein said insecticidal cleansing emulsion system is homogeneous.

12. The insecticidal cleansing emulsion system of claim 1, wherein said insecticidal cleansing emulsion system further comprises a synergist.

13. The insecticidal cleansing emulsion system of claim 1, wherein said metal salt is NaCl.

14. The insecticidal cleansing emulsion system of claim 1, further comprising an antioxidant.

15. The insecticidal cleansing emulsion system of claim 14, wherein said antioxidant is selected from the group consisting of Vitamin E, Vitamin A palmitate, ethoxyquin, propyl gallate, butylated hydroanisole (BHA), butylated hydroxytoluene (BHT), and combinations thereof.

16. The insecticidal cleansing emulsion system of claim 15, wherein said antioxidant is butylated hydroxytoluene (BHT).

17. The insecticidal cleansing emulsion system of claim 1, further comprising an emollient.

18. A method for eradicating insects on a pet, said method comprising:
   administering an insecticidal cleansing emulsion system of claim 1 to a pet,
   wherein upon dilution with water, the anionic surfactant and the cationic polymer form a water-insoluble complex, to eradicate insects on said pet.

\* \* \* \* \*